United States Patent
Ansmann et al.

(10) Patent No.: US 6,228,831 B1
(45) Date of Patent: May 8, 2001

(54) AQUEOUS NACREOUS LUSTRE CONCENTRATES

(75) Inventors: Achim Ansmann, Erkrath; Rolf Kawa, Monheim, both of (DE)

(73) Assignee: Henkel Kommanditgesellschaft auf Aktien, Duesseldorf (DE)

(*) Notice: Subject to any disclaimer, the term of this patent is extended or adjusted under 35 U.S.C. 154(b) by 0 days.

(21) Appl. No.: 09/202,083

(22) PCT Filed: May 30, 1997

(86) PCT No.: PCT/EP97/02824

§ 371 Date: May 6, 1999

§ 102(e) Date: May 6, 1999

(87) PCT Pub. No.: WO97/47274

PCT Pub. Date: Dec. 18, 1997

(30) Foreign Application Priority Data

Jun. 7, 1996 (DE) ............................................. 196 22 968

(51) Int. Cl.⁷ ................................. C11D 1/06; C11D 1/83
(52) U.S. Cl. ......................... 510/416; 510/417; 510/437; 510/505; 510/506
(58) Field of Search ........................... 252/299.7, 136.42, 252/311, 312, 314; 510/130, 159, 416, 505, 506, 125, 122, 437, 417; 426/610; 424/70.1, 70.31; 536/7.2, 7.4

(56) References Cited

U.S. PATENT DOCUMENTS

| | | |
|---|---|---|
| 3,350,320 | 10/1967 | Hewitt ................................. 252/161 |
| 3,547,828 | 12/1970 | Mansfield ............................ 252/351 |
| 3,707,535 | 12/1972 | Lew .................................... 260/210 R |
| 3,772,269 | 11/1973 | Lew .................................... 260/210 R |
| 3,839,318 | 10/1974 | Mansfield ........................... 260/210 R |
| 4,009,254 | 2/1977 | Renold ................................. 424/59 |
| 4,172,887 | 10/1979 | Vanlerberghe et al. ............... 424/70 |
| 4,349,669 | 9/1982 | Klahr et al. ........................... 536/127 |
| 4,777,038 | 10/1988 | Scheuffgen ............................ 424/70 |
| 4,919,923 * | 4/1990 | Hoeffkes et al. ....................... 424/70 |
| 5,213,792 | 5/1993 | Grundmann et al. ................... 424/70 |
| 5,366,654 * | 11/1994 | Van Den Brom et al. ...... 252/174.17 |
| 5,403,508 * | 4/1995 | Reng et al. ....................... 252/174.22 |
| 5,711,899 | 1/1998 | Kawa et al. .......................... 252/311 |

FOREIGN PATENT DOCUMENTS

| | | |
|---|---|---|
| 11 65 574 | 3/1964 | (DE) . |
| 19 43 689 | 3/1970 | (DE) . |
| 20 36 472 | 2/1971 | (DE) . |
| 22 42 541 | 3/1974 | (DE) . |
| 26 03 803 | 8/1977 | (DE) . |
| 30 01 064 | 7/1981 | (DE) . |
| 20 24 051 | 5/1986 | (DE) . |
| 4119890 * | 10/1987 | (DE) . |
| 38 37 860 | 5/1990 | (DE) . |
| 38 43 572 | 6/1990 | (DE) . |
| 41 03 551 | 8/1992 | (DE) . |
| 41 19 890 | 12/1992 | (DE) . |
| 295 20 749 U | 4/1996 | (DE) . |
| 0 077 167 | 4/1983 | (EP) . |
| 0 130 609 | 1/1985 | (EP) . |
| 0 181 773 | 5/1986 | (EP) . |
| 0 205 922 | 12/1986 | (EP) . |
| 264844 * | 10/1987 | (EP) . |
| 0 264 844 | 4/1988 | (EP) . |
| 0 367 939 | 5/1990 | (EP) . |
| 0 407 042 | 1/1991 | (EP) . |
| 0 285 389 | 9/1992 | (EP) . |
| 0 569 843 | 11/1995 | (EP) . |
| 0 684 302 | 11/1995 | (EP) . |
| 0 581 193 | 6/1998 | (EP) . |
| 2 252 840 | 12/1978 | (FR) . |
| 962 919 | 7/1964 | (GB) . |
| 1 333 475 | 10/1973 | (GB) . |
| 63-284113 | 11/1988 | (JP) . |

OTHER PUBLICATIONS

J. Falbe (ed.), "Surfactants in Consumer Products", Springer Verlag, Berlin (1987) pp. 54–124.
J. Falbe (ed.), "Katalysatoren, Tenside und Mineraloeladditive", Thieme Verlag, Stuttgart, (1978), pp. 123–217.
"Kosmetische Fäbemittel", Farbstoffkommission der Deutschen Forschungsgemeinschaft, Verlag Chemie, Weinheim, 1984, pp. 81 to 106.
Chemical Abstract 98:34898n, vol. 98, 1983, p. 680.

* cited by examiner

Primary Examiner—Yogendra Gupta
Assistant Examiner—Gregory E. Webb
(74) Attorney, Agent, or Firm—John E. Drach; Steven J. Trzaska

(57) ABSTRACT

A pearlescent concentrate containing: (a) from 1 to 99.9% by weight of a fatty compound selected from the group consisting of a fatty alcohol, a fatty ketone, a fatty ether, a fatty carbonate, and mixtures thereof, wherein the fatty compound contains at least 18 carbon atoms; (b) from 0.1 to 90% by weight of an emulsifier component selected from the group consisting of an anionic surfactant, a nonionic surfactant, a cationic surfactant, an ampholytic surfactant, a zwitterionic surfactant, and mixtures thereof; and (c) up to 40% by weight of a polyol, all weights being based on the total weight of the concentrate.

18 Claims, No Drawings

AQUEOUS NACREOUS LUSTRE CONCENTRATES

BACKGROUND OF THE INVENTION

This invention relates to aqueous pearlescent concentrates containing selected fatty compounds, emulsifiers and optionally polyols, to a process for their production, to a process for the production of pearlescent surface-active formulations using the concentrates and to the use of the fatty compounds as pearlescent waxes.

For centuries, the softly shimmering luster of pearls has held a particular fascination for human beings. It is therefore no wonder that manufacturers of cosmetic preparations endeavour to give their products an attractive, valuable and rich appearance. The first pearlescence used in cosmetics in the middle ages was a pearlescent paste of natural fish scales. At the beginning of the present century, it was discovered that bismuth oxide chlorides were also capable of producing pearlescence. By contrast, pearlescent waxes, particularly of the glycol monofatty acid ester and difatty acid ester type, are of importance in modern cosmetics, being used mainly for the production of pearlescence in hair shampoos and shower gels. An overview of modern pearlescent formulations was published by A. Ansmann and R. Kawa in Parf. Kosm., 75, 578 (1994).

Various formulations capable of providing surface-active products with the required pearlescence are known from the prior art. For example, German patent applications DE-A1 38 43 572 and DE-A1 41 03 551 (Henkel) describe pearlescent concentrates in the form of free-flowing aqueous dispersions containing 15 to 40% by weight of pearlescent components, 5 to 55% by weight of emulsifiers and 0.1 to 5% by weight or 15 to 40% by weight of polyols. The pearlescent waxes are acylated polyalkylene glycols, monoalkanolamides, linear saturated fatty acids or ketosulfones. European patents EP-B1 0 181 773 and EP-B1 0 285 389 (Procter & Gamble) describe shampoo compositions containing surfactants, non-volatile silicones and pearlescent waxes. European patent application EP-A2 0 205 922 (Henkel) relates to free-flowing pearlescent concentrates containing 5 to 15% by weight of acylated polyglycols, 1 to 6% by weight of fatty acid monoethanolamides and 1 to 5% by weight of nonionic emulsifiers. According to the teaching of European patent EP-B1 0 569 843 (Hoechst), nonionic, free-flowing pearlescent dispersions can also be obtained by preparing mixtures of 5 to 30% by weight of acylated polyglycols and 0.1 to 20% by weight of selected nonionic surfactants. In addition, European patent application EP-A2 0 581 193 (Hoechst) describes free-flowing, preservative-free pearlescent dispersions containing acylated polyglycol ethers, betaines, anionic surfactants and glycerol. Finally, European patent application EP-A1 0 684 302 (Th. Goldschmidt) relates to the use of polyglycerol esters as crystallization aids for the production of pearlescent concentrates.

Despite the large number of formulations, there is a constant need on the market for new pearlescent waxes which, in contrast to acylated polyglycols for example, do not contain any ethylene oxide units and which are distinguished from known products by their brilliant luster, even when used in smaller quantities, so that critical ingredients, such as silicones for example, may also be used without any adverse effect on the stability of the formulations and which, at the same time, contain ester groups, thus guaranteeing adequate biodegradability, and which are free-flowing and hence easy to handle, particularly in concentrated form.

Accordingly, the problem addressed by the present invention was to provide new pearlescent concentrates which would satisfy the complex requirement profile described above.

DESCRIPTION OF THE INVENTION

The present invention relates to aqueous pearlescent concentrates containing—based on the non-aqueous component—
(a) 1 to 99.1% by weight of fatty compounds selected from the group consisting of fatty alcohols, fatty ketones, fatty ethers and fatty carbonates with the proviso that the compounds contain in all at least 18, preferably 24 and more preferably 32 to 48 carbon atoms,
(b) 0.1 to 90% by weight of anionic, nonionic, cationic, ampholytic and/or zwitterionic emulsifiers and
(c) 0 to 40% by weight of polyols,
with the proviso that the quantities add up to 100% by weight.

It has surprisingly been found that the long-chain fatty compounds mentioned have excellent pearlescing properties and are distinguished from known products by greater brilliance, even when used in smaller quantities, particular particle fineness and stability in storage. The pearlescent waxes are readily biodegradable and free-flowing in concentrated form and even enable problematical ingredients, for example silicones, to be incorporated in cosmetic formulations.

Fatty Alcohols

Long-chain fatty alcohols suitable for use as component (a1) correspond to formula (I):

$$R^1OH \qquad (I)$$

in which $R^1$ is a linear alkyl group containing at least 18, preferably 24 to 48 and more preferably 32 to 36 carbon atoms. The compounds mentioned are, for example, behenyl alcohol or oxidation products of long-chain paraffins.

Fatty Ketones

Fatty ketones suitable for use as component (a2) correspond to formula (II):

$$R^2\text{—CO—}R^3 \qquad (II)$$

in which $R^2$ and $R^3$ independently of one another are optionally hydroxysubstituted alkyl and/or alkenyl groups containing 1 to 22 carbon atoms, with the proviso that they contain in all at least 18, preferably 24 and more preferably 32 to 48 carbon atoms. The ketones may be prepared by known methods, for example by pyrolysis of the corresponding fatty acid magnesium salts. The ketones may be symmetrical or non-symmetrical in their structure although the two substituents $R^2$ and $R^3$ preferably differ from one another by only one carbon atom and are derived from fatty acids containing 16 to 22 carbon atoms. Caprinone, laurone and stearone are distinguished by particularly advantageous pearlescent properties.

Fatty Ethers

Component (a3) consists of fatty ethers corresponding to formula (III):

$$R^4\text{—O—}R^5 \qquad (III)$$

in which $R^4$ and $R^5$ independently of one another are alkyl and/or alkenyl groups containing 1 to 22 carbon atoms, with the proviso that they contain in all at least 18, preferably 24 and more preferably 32 to 48 carbon atoms. Fatty ethers of the type mentioned are normally prepared by acidic condensation of the corresponding fatty alcohols. Fatty ethers having particularly advantageous pearlescent properties are obtained by condensation of fatty alcohols containing 16 to 22 carbon atoms, for example cetyl alcohol, cetearyl alcohol, stearyl alcohol, isostearyl alcohol, oleyl alcohol, behenyl alcohol and/or erucyl alcohol. Distearyl ether is particularly preferred.

Fatty Carbonates

Component (a4) consists of fatty carbonates corresponding to formula (IV):

in which $R^6$ and $R^7$ independently of one another are optionally hydroxyfunctionalized alkyl and/or alkenyl groups containing 1 to 22 carbon atoms, with the proviso that they contain in all at least 18, preferably 24 and more preferably 32 to 48 carbon atoms. The compounds are obtained, for example, by transesterifying dimethyl or diethyl carbonate with the corresponding fatty alcohols or hydroxyalcohols using methods known per se. Accordingly, the fatty carbonates may have a symmetrical or non-symmetrical structure. However, carbonates in which $R^6$ and $R^7$ are the same and represent alkyl groups containing 16 to 22 carbon atoms are preferably used. Transesterification products of dimethyl or diethyl carbonate with cetyl alcohol, cetearyl alcohol, stearyl alcohol, isostearyl alcohol, oleyl alcohol, 12-hydroxystearyl alcohol, behenyl alcohol and/or erucyl alcohol in the form of their mono- and diesters and technical mixtures thereof are particularly preferred.

The fatty compounds may be used in quantities of 1 to 99.9% by weight, based on the concentrates, and are normally used in quantities of 5 to 75% by weight, preferably in quantities of 10 to 50% by weight and more preferably in quantities of 15 to 30% by weight.

Emulsifiers

The pearlescent concentrates according to the invention may contain nonionic surfactants from at least one of the following groups as emulsifiers:

(b1) adducts of 2 to 30 moles of ethylene oxide and/0 to 5 moles of propylene oxide with linear fatty alcohols containing 8 to 22 carbon atoms, with fatty acids containing 12 to 22 carbon atoms, with alkylphenols containing 8 to 15 carbon atoms in the alkyl group and with triglycerides;

(b2) $C_{12/18}$ fatty acid monoesters and diesters of adducts of 1 to 30 moles of ethylene oxide with glycerol;

(b3) glycerol monoesters and diesters and sorbitan monoesters and diesters of saturated and unsaturated fatty acids containing 6 to 22 carbon atoms and ethylene oxide adducts thereof;

(b4) alkyl mono- and oligoglycosides containing 8 to 22 carbon atoms in the alkyl group and ethoxylated analogs thereof;

(b5) adducts of 15 to 60 moles of ethylene oxide with castor oil and/or hydrogenated castor oil;

(b6) polyol esters and, in particular, polyglycerol esters such as, for example, polyglycerol polyricinoleate or polyglycerol poly-12-hydroxy-stearate. Mixtures of compounds from several of these classes are also suitable;

(b7) adducts of 2 to 15 moles of ethylene oxide with castor oil and/or hydrogenated castor oil;

(b8) partial esters based on linear, branched, unsaturated and saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(b9) trialkyl phosphates;

(b10) wool wax alcohols;

(b11) polysiloxane/polyalkyl polyether copolymers and corresponding derivatives;

(b12) mixed esters of pentaerythritol, fatty acids, citric acid and fatty alcohol according to DE-PS 11 65 574 and (b13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use as surfactants are known, for example, from U.S. Pat. Nos. 3,839,318, 3,707,535, 3,547,828, DE-OS 19 43 689, DE-OS 20 36 472 and DE-A1 30 01 064 and also from EP-A 0 077 167. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, especially methyl-quaternized difatty acid triethanolamine ester salts, being particularly preferred.

The pearlescent concentrates according to the invention may contain the emulsifiers in quantities of 0.1 to 90% by weight, preferably in quantities of 5 to 50% by weight and, more preferably, in quantities of 10 to 40% by weight.

Polyols

Polyols which may be used as component (c) in accordance with the invention preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

The pearlescent concentrates according to the invention may contain the polyols, preferably glycerol, propylene glycol, butylene glycol, hexylene glycol and polyethylene glycols with an average molecular weight of 100 to 1,000 in quantities of 0.1 to 40% by weight, preferably in quantities of 0.5 to 15% by weight and, more preferably, in quantities of 1 to 5% by weight.

Production Process

In one preferred embodiment, which is also a subject of the invention, the pearlescent concentrates are produced by preparing a mixture of components (a), (b) and (c), heating it to a temperature 1 to 30° C. above the melting point of the mixture, mixing it with the necessary quantity of water having substantially the same temperature and then cooling the mixture to room temperature. In an alternative method of production, a concentrated aqueous (anionic) surfactant paste may be initially introduced, the pearlescent wax stirred in while heating and the mixture subsequently diluted with more water to the required concentration or the mixing step may be carried out in the presence of polymeric hydrophilic thickeners such as, for example, hydroxypropyl celluloses, xanthan gum or polymers of the carbomer type.

Commercial Applications

The pearlescent concentrates according to the invention are suitable for opacifying surface-active formulations such as, for example, hair shampoos or manual dishwashing detergents. Accordingly, the present invention also relates to a process for the production of opacified and pearlescent liquid aqueous preparations of water-soluble surface-active substances, in which the pearlescent concentrates are added to the clear aqueous preparations at 0 to 40° C. in a quantity of 0.5 to 40% by weight and preferably 1 to 20% by weight of the preparation and are dispersed therein by stirring.

Surfactants

The surface-active formulations according to the invention, which have a non-aqueous component of generally 1 to 50 and preferably 5 to 35% by weight, may contain nonionic, anionic, cationic and/or amphoteric or zwitterionic surfactants which may be present in the formulations in quantities of normally about 50 to 99% by weight and preferably 70 to 90% by weight. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotrigly-cerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds and esterquats, more particularly quatemized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217. The same surfactants may also be directly used for the production of the pearlescent concentrates. The anionic surfactants are also suitable as emulsifiers. In this connection, the use of alkyl ether sulfates as anionic emulsifiers is preferred.

Auxiliaries and Additives

The surface-active formulations to which the pearlescent concentrates according to the invention may be added may contain other auxiliaries and additives such as, for example, oils, superfatting agents, stabilizers, waxes, consistency regulators, thickeners, cationic polymers, silicone compounds, biogenic agents, anti-dandruff agents, film-formers, preservatives, hydro-ropes solubilizers, UV absorbers, dyes and fragrances.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer triol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers. The consistency regulators mainly used are fatty alcohols containing 12 to 22 and preferably 16 to 18 carbon atoms. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshafen, FRG), condensation products of polyglycols and amines, quaternized collagen polypeptides such as, for example, Lauryldimonium Hydroxypropyl Hydrolyzed Collagen (Lame-quat®L, Grünau GmbH), quaternized wheat polypeptides, polyethyleneimine, cationic silicone polymers such as, for example, Amidomethicone or Dow Corning, Dow Corning Co., USA, copolymers of adipic acid and dimethylaminohydroxypropyl diethylenetriamine (Cartaretine®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example, bis-dimethylamino-1,3-propane, cationic guar gum such as, for example, Jaguar®CBS, Jaguar®C-17, Jaguar®C-16 of Celanese, USA, quaternized ammonium salt polymers such as, for example, Mirapol® A-15, Mirapol® AD-1, Mirapol® AZ-1 of Miranol, USA.

Suitable silicone compounds are, for example, dimethyl polysiloxanes, methylphenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, paraffin wax or microwaxes, optionally in combination with hydrophilic waxes, for example cetyl stearyl alcohol. Besides the hydroxycarboxylic acid esters, other known pearlescent waxes such as, in particular, mono- and difatty acid esters of polyalkylene glycols, partial glycerides and triglycerides and esters of fatty alcohols with polybasic carboxylic acids and hydroxycarboxylic acids may also be used for the purposes of the invention. Metal salts of fatty acids such as, for example, magnesium, aluminium and/or zinc stearate may be used as stabilizers. In the context of the invention, biogenic agents are, for example, bisabolol, allantoin, phytantriol, panthenol, AHA acids, plant extracts and vitamin complexes. Climbazol, octopirox and zinc pyrethion may be used as antidandruff agents. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. In addition, hydrotropes such as, for example, ethanol, isopropyl alcohol, propylene glycol or glucose may be used to improve flow behavior. Suitable preservatives are, for example, phenoxyethanol, formaldehyde solution, parabens, pentanediol or sorbic acid. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total content of auxiliaries and additives may be from 1 to 50% by weight and is preferably from 5 to 40% by weight, based on the formulation. The formulations may be produced by standard cold or hot processes and are preferably produced by the phase inversion temperature method.

Finally, the present invention relates to the use of the fatty compounds mentioned as pearlescent waxes for the production of surface-active formulations.

EXAMPLES

Pearlescent concentrates R1 to R7 according to the invention and comparison mixture R8 were stored for 14 days at 40° C., after which their viscosities were measured by the Brookfield method using an RVT viscosi-meter (23° C., 10 r.p.m., spindle 5). Water-containing hair shampoos each containing 2 g of pearlescent concentrates R1 to R7, 15 g of coconut fatty alcohol+2 EO sulfate sodium salt, 3 g of dimethyl polysiloxane, 5 g of cocoalkyl glucoside and 1.5 g of an esterquat (water to 100% by weight) were then prepared by mixing the ingredients at 20° C. The particle fineness of the pearlescent crystals in the shampoos was visually evaluated under a microscope on a scale of 1=very fine crystals to 5=coarse crystals. Pearlescence was also evaluated on a scale of 1=brilliant to 5=dull. Opacity was visually determined and was evaluated as (+)=opaque or (−)=non-opaque. The compositions and results are set out in Table 1 where all quantities are expressed as percentages by weight.

TABLE 1

Composition and Performance of Pearlescent Concentrates

| Composition | R1 | R2 | R3 | R4 | R5 | R6 | R7 | R8 |
|---|---|---|---|---|---|---|---|---|
| $C_{32/48}$ Fatty alcohol | 25 | – | 20 | 20 | – | – | – | – |
| Stearone | – | 25 | – | – | – | – | – | – |
| Distearyl ether | – | – | – | – | 25 | – | 7 | – |

TABLE 1-continued

Composition and Performance of Pearlescent Concentrates

| Composition | R1 | R2 | R3 | R4 | R5 | R6 | R7 | R8 |
|---|---|---|---|---|---|---|---|---|
| Mono/distearyl carbonate | – | – | – | – | – | 25 | – | – |
| Ethylene glycol distearate | – | – | 5 | 5 | – | – | – | 25 |
| Cocoalcohol + 4EO | 5 | 5 | 5 | – | 5 | 5 | – | 5 |
| Cocoalkyl glucoside | 9 | 9 | 9 | 15 | 9 | 9 | – | 9 |
| Cocofatty acid betaine | 5 | 5 | 5 | 4 | 5 | 5 | – | 5 |
| Cocoalcohol + 2EO sulfate Na salt | – | – | – | – | – | – | 65 | – |
| Glycerol | 5 | 5 | 5 | 5 | 5 | 5 | 4 | 5 |
| Propylene glycol/butylene glycol (1:5) | – | – | – | – | – | – | 23 | – |
| Water | \multicolumn{8}{c}{To 100} | | | | | | | |
| Viscosity of the concentrates [mPas] | | | | | | | | |
| - After 1 d, 40° C. | 8,100 | 8,200 | 6,400 | 7,900 | 8,100 | 8,100 | 8,300 | 9,500 |
| - After 14 d, 40° C. | 7,900 | 7,800 | 5,900 | 7,800 | 7,800 | 7,700 | 8,100 | 7,200 |
| Pearlescence in the formulation | | | | | | | | |
| - Luster | 1.5 | 1.5 | 1.0 | 1.0 | 1.5 | 1.5 | 1.0 | 2.0 |
| - Particle fineness | 1.5 | 1.5 | 1.5 | 2.0 | 1.5 | 1.0 | 1.0 | 3.0 |
| - Opacity | – | – | – | – | – | – | – | + |

What is claimed is:

1. A pearlescent concentrate comprising:
   (a) from 15 to 30% by weight of a fatty compound selected from the group consisting of a fatty alcohol, a fatty ketone, a fatty ether, a fatty carbonate, and mixtures thereof, wherein the fatty compound contains at least 18 carbon atoms;
   (b) from 10 to 40% by weight of an emulsifier component selected from the group consisting of an anionic surfactant, a nonionic surfactant, a cationic surfactant, an ampholytic surfactant, a zwitterionic surfactant, and mixtures thereof; and
   (c) 0.1 to 40% by weight of a polyol, all weights being based on the total weight of the concentrate.

2. The concentrate of claim 1 wherein the fatty compound is a fatty alcohol having from 18 to 48 carbon atoms.

3. The concentrate of claim 1 wherein the fatty compound is a fatty ketone.

4. The concentrate of claim 1 wherein the fatty compound is a fatty ether.

5. The concentrate of claim 1 wherein the fatty compound is a fatty carbonate.

6. The concentrate of claim 1 wherein the emulsifier component is an alkyl ether sulfate.

7. The concentrate of claim 1 wherein the polyol is selected from the group consisting of glycerol, 1,2-propylene glycol, butylene glycol, hexylene glycol, polyethylene glycol, and mixtures thereof, and wherein the polyol has an average molecular weight of from 100 to 1,000 dalton.

8. The concentrate of claim 1 wherein the polyol is present in the concentrate in an amount of from 1 to 5% by weight, based on the weight of the concentrate.

9. A cleaning composition containing from 0.5 to 40% by weight of the pearlescent concentrate of claim 1.

10. A process for opacifying a cleaning composition comprising adding, at a temperature of from 0 to 40° C., from 0.5 to 40% by weight of the pearlescent concentrate of claim 1 to the cleaning composition.

11. A process for making a pearlescent concentrate comprising:
   (a) providing from 1 to 99.9% by weight of a fatty compound selected from the group consisting of a fatty alcohol, a fatty ketone, a fatty ether, a fatty carbonate, and mixtures thereof, wherein the fatty compound contains at least 18 carbon atoms;
   (b) providing from 0.1 to 90% by weight of an emulsifier component selected from the group consisting of an anionic surfactant, a nonionic surfactant, a cationic surfactant, an ampholytic surfactant, a zwitterionic surfactant, and mixtures thereof;
   (c) providing up to 40% by weight of a polyol, all weights being based on the total weight of the concentrate;
   (d) mixing (a)–(c) to form a mixture;
   (e) heating the mixture to a temperature of from 1 to 30° C. above a melting point of the mixture;
   (f) adding water to the mixture, with stirring, having substantially the same temperature as the mixture; and
   (g) cooling the mixture to room temperature to form the pearlescent concentrate.

12. The process of claim 11 wherein the fatty compound is a fatty alcohol having from 18 to 48 carbon atoms.

13. The process of claim 11 wherein the fatty compound is a fatty ketone.

14. The process of claim 11 wherein the fatty compound is a fatty ether.

15. The process of claim 11 wherein the fatty compound is a fatty carbonate.

16. The process of claim 11 wherein the fatty compound is present in the concentrate in an amount of from 15 to 30% by weight, based on the weight of the concentrate.

17. The process of claim 11 wherein the emulsifier component is present in the concentrate in an amount of from 10 to 40% by weight, based on the weight of the concentrate.

18. The process of claim 11 wherein the polyol is present in the concentrate in an amount of from 1 to 5% by weight, based on the weight of the concentrate.

* * * * *